United States Patent [19]

Rohling et al.

[11] Patent Number: 5,290,266

[45] Date of Patent: Mar. 1, 1994

[54] FLEXIBLE COATING FOR MAGNETIC RESONANCE IMAGING COMPATIBLE INVASIVE DEVICES

[75] Inventors: Kenneth W. Rohling, Burnt Hills; Lionel M. Levinson, Schenectady, both of N.Y.

[73] Assignee: General Electric Company, Schenectady, N.Y.

[21] Appl. No.: 929,350

[22] Filed: Aug. 14, 1992

[51] Int. Cl.⁵ .............................................. A61M 5/32
[52] U.S. Cl. ................................ 604/272; 604/273; 128/653.2; 427/2
[58] Field of Search .............. 604/272, 273, 264, 265, 604/280, 266, 282; 128/653.2, 653.4; 427/516, 207.1, 2

[56] References Cited

U.S. PATENT DOCUMENTS 3,695,921 10/1972 Shepherd et al. ........................ 427/2
5,019,096 5/1991 Fox, Jr. et al. .......................... 623/1

OTHER PUBLICATIONS

"Medical Product Manufacturing News" published by Canon Communications, 3340 Ocean Park Blvd., Suite 1000, Santa Monica, Calif. 90405, p. 12 of the Jul./Aug. 1992 issue.

*Primary Examiner*—C. Fred Rosenbaum
*Assistant Examiner*—Vanitha Alexander
*Attorney, Agent, or Firm*—Lawrence P. Zale; Marvin Snyder

[57] ABSTRACT

Invasive devices, such as laser fiber guides and biopsy needles, constructed of a material which exhibits little or no magnetic susceptibility, have a flexible polymer coating for retaining pieces of the device in the event of a fracture of the invasive device. The polymer coating also allows removal of the pieces of a fractured invasive device from the body of a subject without requiring surgery. The surgical instruments can be used inside a magnetic field during magnetic resonance (MR) imaging, thereby allowing interactive internal images to be produced and displayed to a surgeon during surgery. Since the invasive devices exhibit low susceptibility, they do not distort a created MR image.

14 Claims, 1 Drawing Sheet

FLEXIBLE COATING FOR MAGNETIC RESONANCE IMAGING COMPATIBLE INVASIVE DEVICES

CROSS REFERENCE TO RELATED APPLICATIONS

This application is related to U.S. patent application "MAGNETIC RESONANCE COMPATIBLE SURGICAL INSTRUMENTS" Ser. No. 07/930,954 Kenneth W. Rohling, Steven P. Souza, John F. Schenck, Ronald D. Watkins and Christopher J. Hardy filed Aug. 17, 1992, now abandoned, assigned to the present assignee and hereby incorporated by reference.

BACKGROUND OF THE INVENTION

1. Field of the Invention

This invention relates to invasive medical apparatus, and more specifically to surgical instruments which can be used safely during magnetic resonance imaging.

2. Description of Related Art

A biopsy needle is an invasive device used in surgical procedures to penetrate a subject in order to reach a desired tissue and extract a small portion of the tissue for analysis. Another invasive device, a laser fiber guide, is a hollow tube also used in surgical procedures to penetrate a subject to a desired location, and when at that location, an optical fiber can be inserted through the laser fiber guide with one end positioned at the desired location. Optical radiation, such as laser radiation, is introduced at another end of the optical fiber so as to pass through the fiber and impinge on tissue at the desired location for the purpose of cauterizing or destroying the tissue at that location. These biopsy needles and fiber guides must be thin enough to penetrate the subject, stiff enough not to bend, made of a material which can be sterilized and does not cause a significant adverse physiological reaction when introduced into a living subject. Conventional invasive devices are constructed of a material, usually metal, such as stainless steel. Several other alloys are well suited for the construction of such invasive devices.

Magnetic resonant (MR) imaging employs large magnets for creating a homogeneous magnetic field, and gradient coils for altering the magnetic field in a uniform manner in time or space, creating magnetic field gradients. MR imaging also employs radiofrequency (RF) coils for applying an RF field to tissue to be imaged, causing the tissue to resonate and create an MR response signal. The MR response signal is used to construct an image. The degree of homogeneity of the magnetic field and the linearity of a magnetic field gradient over space are important in creating a clear, undistorted image. Interference with the RF field also reduces the quality of the created image.

Recently, there is a desire to create interactive images of internal organs of a patient during surgery. Since magnetic resonance imaging provides great detail in images of soft tissues, it is advantageous to use MR imaging. The best imaging results when surgical equipment does not interfere with the magnetic and RF fields created by the MR imaging equipment.

Many metals are ferromagnetic and are physically pulled toward a magnet. Since the magnetic field employed in MR imaging is large, an amount of magnetic force applied to the equipment can be large. Invasive devices, therefore, should not be made of a ferromagnetic material since a magnetic force would be applied to them causing them to be difficult to manipulate.

Other problems occur with materials in which eddy currents are produced when placed in a variable magnetic field. The eddy currents in these materials, usually conductors, create their own magnetic field which interferes with the RF field used for MR imaging. Therefore, materials which exhibit eddy currents, such as aluminium and copper, should not be used within a variable magnetic field.

The degree of magnetization the material exhibits per applied magnetic field is defined as susceptibility. The susceptibility of a material also affects the homogeneity of the applied magnetic field in a region surrounding the material. This can create large distortions in an MR image near the material.

Many materials used for invasive devices which do not exhibit significant susceptibility tend to be brittle and would be likely to fracture when inserted into a subject. This would cause pieces of the device to remain in the subject and not be easily removed. Surgery would likely be the only method of removing such pieces.

Currently, there is a need for surgical instruments which can be used within a MR magnetic field and not be physically pulled toward the magnet creating the MR field, not interfere with a created MR image, and not present a danger of breakage when inserted into a subject.

SUMMARY OF THE INVENTION

Invasive devices used for surgery on a subject, such as biopsy needles and laser fiber guides, constructed of a material having low susceptibility, such as a high-strength ceramic material, are covered with a tough, flexible coating so as to retain all pieces of the invasive device in the event of fracture of the device. Since the invasive devices have little or no magnetic susceptibility, they may be used effectively during magnetic resonance imaging without distorting the image, thereby allowing interactive internal images to be produced and displayed to a surgeon during surgery.

OBJECTS OF THE INVENTION

It is an object of the present invention to provide an invasive device which can be used inside a magnetic field of a magnetic resonance (MR) imaging system and that will remain in one piece even when fractured.

It is another object of the present invention to provide an invasive device which can be safely used in the magnet of a magnetic resonant imaging system which exhibits low susceptibility and does not distort the MR image.

It is another object of the present to provide an invasive device intended to be inserted into a subject situated within a magnetic field of a magnetic resonant imaging system and which will not leave pieces of the invasive device within the subject if the invasive device fractures and is withdrawn from the subject.

BRIEF DESCRIPTION OF THE DRAWING

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which the single FIGURE is a plan view of a biopsy needle constructed of a high-strength ceramic having a flexible coating according to the present invention.

DETAILED DESCRIPTION OF THE INVENTION

Figure 1:
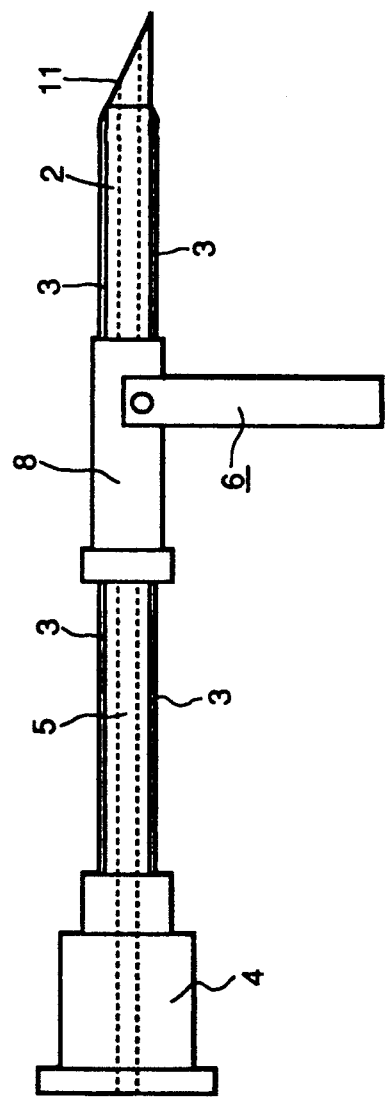

A biopsy needle is shown in the FIGURE and constructed of a cannula 2 having a central opening 5 passing though the length of the cannula 2. Cannula 2 should be constructed of a material which can be sterilized, and is bio-compatible. A bio-compatible material is one which is not toxic, does not cause significant adverse physiological reactions. The cannula may be constructed of a high-strength ceramic material such as yttria ($Y_2O_3$) stabilized zirconia ($ZrO_2$) or magnesia (MgO) stabilized zirconia.

Cannula 2 is covered with a flexible, yet durable coating 3, such as a polymer coating. The coating should also be biocompatible. Cannula 2 and sleeve 3 fit through a sleeve 8 of a positioner 6 and ends in a sharpened end 11. The positioner 6 holds cannula 2 in the proper position so it may be inserted into a subject. Cannula 2 is attached to a luerlock fitting 4 for connection to other surgical apparatus such as a suction device. The biopsy needle is inserted into the subject by penetrating the subject's tissue with sharpened end 11 in order to retrieve a small sample which is collected by vacuum or suction at opening 5. The biopsy needle is then removed from the patient and the sample retained in opening 5 is extracted for tests. To reduce the invasiveness of the procedure, the biopsy needle is made as thin as possible; this requires that the biopsy needle must be constructed of a material having a great degree of strength and rigidity.

In the event that cannula 2 fractures inside a subject, as might be the case when it strikes a bone or is flexed past its allowable range, flexible coating 3 will securely retain the pieces of the cannula.

Materials such as high-strength ceramics used to construct cannula 2 must be very durable, but are more prone to fracture than metals used in constructing conventional biopsy needles. Therefore, flexible coating 3 is applied to retain pieces in the event of fracture. Without the coating, pieces would remain inside the subject when the remainder of the needle is withdrawn from the subject, probably requiring surgery to remove them.

Polymers, such as extruded thermoplastic polyester, can be formed into tubing having walls as thin as 0.0002 inches (5 mm.), having tensile strength of 50,000 psi, and a burst pressure of 600 psi., as described on p. 12 of the July/Aug. 1992 issue of "Medical Product Manufacturing News" published by Canon Communications 3340 Ocean Park Blvd., Suite 1000, Santa Monica, Calif. 90405. This specific polymer is sterilizable by irradiation with gamma rays.

The flexible coating can be applied to an invasive devices by:

1) sterilizing the coating material to be be applied;
2) inserting the invasive device into the coating material; and
3) causing the coating to shrink and tightly conform to the invasive device.

The coating, usually in the form of a tube, is placed over the invasive device so as to cover substantially all of the invasive device. The coating, if heat shrinkable, such as modified polyolefin manufactured by Raychem Corp. Menlo Park Calif. 94025, is then shrunk by heating using, for example, infra-red radiation, insertion into a heated oven, or hot air convection from a blower. The coating, by shrinking, conforms itself to the surface of, and secures, the invasive device.

Alternatively, an adhesive coating may be applied either to the inside of the coating or to the outside of the invasive device prior to assembly in order to tightly affix them to each other.

Another method of applying a flexible coating involves:

1) dissolving the coating material, such as polycarbonate in a solvent;
2) applying the solution to the invasive device by spraying, painting or dipping the invasive device; and
3) drying the invasive device so as to leave a flexible coating on the device.

Still another method involves:

1) heating the coating material which here may comprise for example, an epoxy polymer;
2) applying the non-viscous coating material to the invasive device by spraying, painting or dipping the invasive device; and
3) allowing the polymer to cure so as to leave a flexible coating on the device.

The coating and invasive device may be sterilized by exposure to gamma radiation or sterilizing gases such as ethylene oxide. The sterilizing gas must not be one which causes deterioration of the coating.

If the coating is a heat shrinkable polymer, sterilization by autoclave is unacceptable. However, plastics which can shrink when exposed to radiation or chemical solutions and are unaffected by heat, may be sterilized in an autoclave.

Any instruments which may be required in surgery, such as, but not limited to biopsy needles, optical fiber guides, retractors, clamps, syringes, catheters, laparoscopes, and endoscopes may be constructed according to the requirements set forth for the biopsy needle above.

While several presently preferred embodiments of the present novel invention has been described in detail herein, many modifications and variations will now become apparent to those skilled in the art. It is our intent, therefore, to be limited only by the scope of the appending claims and not to the specific details and instrumentalities presented by way of explanation herein.

What is claimed is:

1. A medical invasive device intended for insertion into a subject immersed in a magnetic field during magnetic resonance imaging comprising a substantially rigid non-metallic material capable of shattering exhibiting a magnetic susceptibility in the magnetic field substantially equal to that of the subject being imaged, so as to cause minimal distortion in a magnetic resonance image, said device having an outer coating of a flexible material having a tensile strength capable of containing pieces of the device in the event of a fracture and allowing removal of all pieces of the invasive device from the subject when the device is withdrawn from the subject.

2. The medical invasive device as recited claim 1 wherein the coating comprises a sterilizable polymer exhibiting a flexibility which allows contortion without rupture and a tensile strength which resists rupture by sharp pieces of the device in the event of a fracture.

3. The medical invasive device as recited claim 2 wherein the coating comprises a polymer which does not cause a significant adverse physiological reaction in a subject when introduced into a subject.

4. A method of producing a shatter-resistant invasive device intended to be used during magnetic resonance (MR) imaging of a subject and having a coating of a flexible material having a tensile strength capable of containing all pieces of the device in event of it fracturing comprising the steps of:
   a) constructing an invasive device of a rigid material capable of shattering and having a magnetic susceptibility substantially equal to that of said subject being imaged;
   b) placing shrinkable tubing of a material being flexible and having substantial tensile strength to contain sharp pieces of the invasive device in the event of fracture, over the invasive device substantially enclosing the invasive device; and
   c) shrinking the tubing causing it to form a coating which tightly conform to the invasive device.

5. The method of producing a shatter-resistant invasive device as recited in claim 4 further comprising the step of applying an adhesive to an inside surface of the tubing prior to step "c".

6. The method of producing a shatter-resistant invasive device as recited in claim 4 further comprising the step of applying an adhesive to an outside surface of the invasive device prior to step "c".

7. The method of producing a shatter-resistant invasive device as recited in claim 4, further comprising the step of sterilizing the tubing.

8. The method of producing a shatter-resistant invasive device as recited in claim 4 further comprising the step of sterilizing the invasive device and tubing.

9. A method of producing a shatter-resistant invasive device intended to be used during magnetic resonance (MR) imaging of a subject and having a coating of a flexible material having a tensile strength capable of containing all pieces of the device in event of its fracture comprising the steps of:
   a) constructing an invasive device of a substantially rigid material capable of shattering having a magnetic susceptibility substantially similar to that of said subject;
   b) dissolving a flexible coating material in a solvent to form a solution;
   c) applying the solution to the invasive device by spraying, painting or dipping the invasive device; and
   d) drying the invasive device so as to leave a tightly conforming flexible coating on the invasive device.

10. The method of producing a shatter-resistant invasive device as recited in claim 9 further comprising the step of sterilizing the invasive device and the flexible coating.

11. A method of producing a shatter-resistant invasive device intended to be used during magnetic resonance (MR) imaging of a subject and having a coating of a flexible material having a tensile strength capable of containing all pieces of the device in event of its fracture comprising the steps of:
   a) constructing an invasive device of a substantially rigid material capable of shattering having a magnetic susceptibility substantially similar to that of said subject;
   b) heating a flexible coating material into a non-viscous state;
   c) applying the coating material to the invasive device by spraying, painting or dipping the invasive device; and
   d) allowing the coating to cure so as to leave a tightly conforming flexible coating on said invasive device.

12. The medical invasive device of claim 1 wherein the rigid non-metallic material is a high strength ceramic material.

13. The medical invasive device of claim 12 wherein the high strength material is yttria ($Y_2O_3$) stabilized zirconia ($ZrO_2$).

14. The medical invasive device of claim 12 wherein the high strength material is magnesia (MgO) stabilized zirconia ($ZrO_2$).

* * * * *